United States Patent [19]

Fallon et al.

[11] Patent Number: 5,552,305
[45] Date of Patent: Sep. 3, 1996

[54] BIOCATALYTIC CONVERSION OF AZOBISNITRILES TO CYANOAMIDES OR DIAMIDES USING PSEUDOMONAS, RHODOCOCCUS OR BREVIBACTERIUM

[75] Inventors: Robert D. Fallon, Elkton, Md.; Ernest B. Wysong, Hockessin, Del.

[73] Assignee: E. I. Du Pont de Nemours and Company, Wilmington, Del.

[21] Appl. No.: 413,529

[22] Filed: Mar. 30, 1995

[51] Int. Cl.[6] .................. C12P 13/02; C12P 13/04; C12P 17/00
[52] U.S. Cl. .................. 435/129; 435/106; 435/117
[58] Field of Search .................. 435/129, 106, 435/117, 280

[56] References Cited

U.S. PATENT DOCUMENTS

| 4,315,856 | 2/1982 | Moore, Jr. ................ 260/192 |
| 4,343,899 | 8/1982 | Watanabe et al. .......... 435/129 |
| 4,629,700 | 12/1986 | Prevatt et al. ........... 435/128 |
| 4,637,982 | 1/1987 | Yamada et al. ............ 435/129 |
| 5,200,331 | 4/1993 | Kawakami et al. .......... 435/129 |
| 5,318,908 | 6/1994 | Seki et al. ............. 435/253.3 |
| 5,326,702 | 7/1994 | Endo et al. .............. 435/129 |

FOREIGN PATENT DOCUMENTS

| 2010929 | 12/1990 | Canada . |
| 0178106 | 4/1986 | European Pat. Off. . |
| 0356912 | 3/1990 | European Pat. Off. . |
| 2154692 | 7/1988 | Japan . |
| WO86/07386 | 12/1986 | WIPO . |

OTHER PUBLICATIONS

Eder E. et al., Toxicol. Lett. 48:225–34 (1989).

*Primary Examiner*—Michael G. Wityshyn
*Assistant Examiner*—S. Saucier

[57] ABSTRACT

A process for the enzymatic conversion of azobisnitriles to water soluble cyanoamide and diamide derivatives utilizing the enzymatic apparatus of nitrile hydratase contained in bacteria is disclosed.

13 Claims, No Drawings

BIOCATALYTIC CONVERSION OF AZOBISNITRILES TO CYANOAMIDES OR DIAMIDES USING PSEUDOMONAS, RHODOCOCCUS OR BREVIBACTERIUM

The present invention comprises a process for the biotransformation of azobisnitriles into more water soluble derivatives. More specifically, microorganisms containing nitrile hydrarase are used to convert azobisnitriles into water soluble cyanoamide or diamide derivatives.

BACKGROUND

The hydrolysis of nitriles has long been useful for the production of various amide intermediates in processes for making polymers such as nylon and acrylamide. Processes involving enzymatic conversion of nitrile substrates are sometimes favored over chemical synthesis, for their production of fewer harmful reaction by-products and for greater reaction specificity. The occurrence of nitrile hydrolyzing enzymes has been widely described. Within this family of enzymes, two broad classes are generally recognized. The first includes the nitrile hydratases which bring about the addition of one molecule of water to the nitrile, resulting in the formation of the amide free product:

Reaction 1

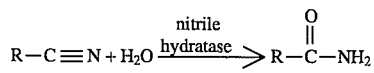

The second group includes the nitrilases which bring about the addition of two molecules of water to the nitrile resulting in formation of the acid free product plus ammonia:

Reaction 2

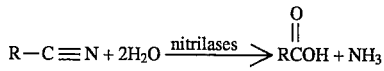

A wide range of nitriles are amenable to conversion via Reaction 1 or Reaction 2. Recent reviews have disclosed a diversity of amenable substrates for nitrile hydrolyzing enzymes found in bacterial genera such as Rhodococcus, Pseudomonas, Alcaligenes, Arthrobacter, Bacillus, Bacteridium, Brevibacterium, Corynebacterium, and Micrococcus.

The enzymatic hydrolysis of aliphatic nitriles and their derivatives by methods employing bacterial strains of the above mentioned genera is well known. For example U.S. Pat. No. 4,637,982 of Yamada et al. published Jan. 20, 1987, teaches a process for enzymatic hydration of aliphatic nitriles having 2 to 4 carbon atoms to the corresponding amide using a strain of Pseudomonas. European Patent 178 106 published Apr. 16, 1986, discloses selective transformation of one of the cyano groups of a dinitrile to the corresponding carboxylic acid, amide, ester or thioester using a mononitrilase.

Another class of nitriles that have found commercial utility in polymer synthesis are the azobisnitriles. One class of azobisnitriles of industrial interest are those capable of reacting to form organic free radicals and/or nitrogen gas, such as 2,2'-azobis (2-methylpropionitrile). These find utility as free radical polymerization initiators and/or blowing agents for polymer foams via the following reaction:

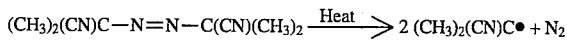

A disadvantage of many azobisnitriles is their low water solubility. This reduces their utility as free radical polymerization initiators and blowing agents for polymer foams in aqueous based polymer formulations. A number of chemical synthetic methods have been developed for the conversion of azobisnitriles to more water soluble derivatives. However, azobisnitriles are known to be unstable in the presence of biological organisms due to the nitrogen-nitrogen double bond. Azobis-nitriles have not been previously demonstrated to be amenable to attack by nitrile hydratase, amidase or nitrilase enzymes without reduction of the nitrogen-nitrogen double bond. Thus a need exists for converting azobisnitriles to more water soluble derivatives using enzymatic conversion to avoid the harmful reaction by-products of chemical conversions.

Applicants' invention provides a process to readily convert azobisnitriles to their cyanoamide or diamide derivatives via Reaction 1, using the enzymatic apparatus of bacteria of the genera Rhodococcus, Pseudomonas, Alcaligenes, Arthrobacter, Bacillus, Bacteridium, Brevibacterium, Corynebacterium, and Micrococcus. The enzymes may be contained within whole cells or be supplied in a semipurified or purified form. Immobilized forms of the whole cells or enzymes will also carry out the reaction.

SUMMARY OF THE INVENTION

The present invention comprises a process for the enzymatic conversion of an azobisnitrile of formula I:

$$\begin{array}{ccc} CN & & CN \\ | & & | \\ R_1-C-N=N-C-R_3 \\ | & & | \\ R_2 & & R_4 \end{array}$$

where in,

R₁, R₂, R₃ and R₄ are each independently unsubstituted $C_1$–$C_8$ aliphatic hydrocarbon; $C_1$–$C_8$ aliphatic hydrocarbon substituted with carboxyl, hydroxyl, halogen, or—$OR_5$ wherein $R_5$ is a $C_1$–$C_4$ aliphatic hydrocarbon; $C_3$–$C_8$ alicyclic hydrocarbon; $C_3$–$C_8$ alicyclic hydrocarbon substituted with alkyl or halogen; or $C_4$–$C_{10}$ aromatic hydrocarbon substituted with halogen or nitro; a five or six membered heterocyclic ring containing O, S or N atoms; or $R_1$ and $R_2$ or $R_3$ and $R_4$ together with an adjacent carbon atom independently form a $C_4$–$C_{12}$ alicyclic hydrocarbon; said process comprising 1) contacting an aqueous suspension of an azobisnitrile of formula I with a microorganism containing nitrile hydratase 2) producing a cyanoamide of formula II

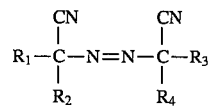

wherein $R_1$, $R_2$, $R_3$ and $R_4$ are defined as above for formula I, or a diamide of formula III

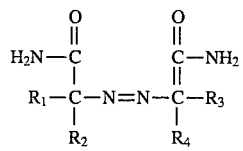

wherein $R_1$, $R_2$, $R_3$ and $R_4$ are defined as above for formula I.

DETAILED DESCRIPTION OF THE INVENTION

Azobisnitriles represent a chemical structure not previously demonstrated to be amenable to attack by nitrile hydratase, amidase or nitrilase enzymes. Because azobisnitriles contain a nitrogen-nitrogen double bond, these compounds are unstable in the presence of biological organisms. To efficiently function in their role as free-radical initiators, azobisnitriles must contain CN groups bound to the carbon directly attached to the N=N bond. This creates the possibility for resonance structures in the region not common to previously described substrate compounds. In addition, the CN group is located on a tertiary carbon. Thus, there is greater steric hindrance at the site of enzyme attack. Nitrile hydratases have often been reported to have lessened activity or undetectable activity for tertiary nitrile attack versus less hindered structures. The present invention provides a process for the biotransformation of azobisnitriles into their more water soluble derivatives without destroying the N=N bond.

In the context of the present disclosure, the azobisnitriles and their products derived via microbial hydrolysis are referred to by the following abbreviations:

AZMPN=2,2'-azobis (2-methylpropionitrile), $(CH_3)_2(CN)$ C—N=N—C(CN) $(CH_3)_2$ AZMPNAm=2(2-azo-2-methylpropionitrile)-2-methylpropionamide, $(CH_3)_2(CN)$ C—N=N—C(C(O)NH$_2$) $(CH_3)_2$ AZMPAm=2,2'-azobis (2-methylpropionamide), $(CH_3)_2(C(O)NH_2)$C—N=N—C(C(O)NH2) $(CH_3)_2$ AZMBN=2,2'-azobis (2-methylbutyronitrile), $C_2H_5(CH_3)$ (CN)C—N=N—C(CN) $(CH_3)$ $C_2H_5$ AZMBNAm=2(2-azo-2-methylbutyronitrile)-2-methylbutyramide, $C_2H_5(CH_3)$ (CN)C—N=N—C(C(O)NH$_2$) $(CH_3)C_2H_5$ AZMBAm=2,2'-Azobis (2-methylbutyramide), $C_2H_5(CH_3)$ $(C(O)NH_2)$C—N=N—C(C(O)NH$_2$) $(CH_3)C_2H_5$ The term "nitrile hydratase" as used herein refers to an enzyme present in a diverse group of bacteria which is capable of catalyzing the addition of one molecule of water across the cyano triple bond of a nitrile compound to give free amide products.

The term "azobisnitrile" as used herein refers to compounds of formula I:

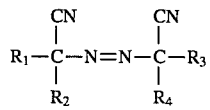

wherein $R_1$, $R_2$, $R_3$ and $R_4$ are defined as above.

The term "cyanoamide derivative" refers to the product of enzymatic hydrolysis wherein one of the two nitrile groups has been hydrolyzed having the general formula II:

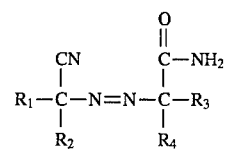

wherein $R_1$, $R_2$, $R_3$ and $R_4$ are the same as defined in the parent azobisnitrile of formula I.

The term "diamide derivative" refers to the product of enzymatic hydrolysis wherein both of the two nitrile groups have been hydrolyzed having the general formula III:

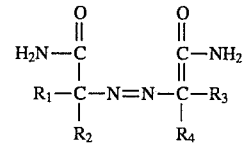

wherein $R_1$, $R_2$, $R_3$ and $R_4$ are the same as defined in the parent azobisnitrile of formula I.

The present invention comprises a process for the enzymatic conversion of azobisnitriles of formula I to more water soluble cyanoamide and diamide derivatives of formulae II and III, respectively. Substrates useful in the present method are azobisnitriles corresponding to the general formula I:

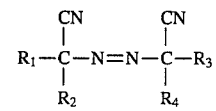

wherein, $R_1$, $R_2$, $R_3$ and $R_4$ are each independently unsubstituted $C_1$–$C_8$ aliphatic hydrocarbon; $C_1$–$C_8$ aliphatic hydrocarbon substituted with carboxyl, hydroxyl, halogen, or —OR$_5$ wherein $R_5$ is a $C_1$–$C_4$ aliphatic hydrocarbon; $C_3$–$C_8$ alicyclic hydrocarbon; $C_3$–$C_8$ alicyclic hydrocarbon substituted with alkyl or halogen; $C_4$–$C_{10}$ aromatic hydrocarbon substituted with halogen or nitro; or a five or six membered heterocyclic ring containing O, S or N atoms; or $R_1$ and $R_2$ or $R_3$ and $R_4$ together with an adjacent carbon atom independently form a $C_4$–$C_{12}$ alicyclic hydrocarbon.

Aliphatic hydrocarbon is used herein to mean linear or branched alkyl, alkenyl and alkynyl groups or a combination thereof. Examples include methane, ethane, propane, butane, pentane, hexane, heptane, octane, ethylene, propylene, butene, pentene, hexene, heptene, octene, acetylene, propyne, butyne, pentyne, hexyne, heptyne and octyne. Alicyclic hydrocarbon is used herein to mean a ring having 3 to 12 carbon atoms and no heteroatoms such as cycloalkanes, cycloalkenes, and cyclodienes. Examples include, among others, cyclopropane, cyclobutane, cyclopentane, cycloheptane, cyclooctane, cyclopropene, cyclobutene, cyclopentene, cyclohexene, cycloheptene, cyclooctene, cyclopentadiene, cyclohexadiene and the like. Aromatic hydrocarbon is used herein to mean hydrocarbons having resonance. Examples include benzene and naphthalene.

Heterocyclic rings include five or six membered rings containing O, S or N atoms. Examples include, among others, furan, thiophene, pyrrole, pyrazole, imidazole, triazole, dithiole, oxathiole, oxazole, thiazole, oxadiazole, dioxazole, oxathiazole, pyran, dioxin, pyridine, pyridazine, pyrimidine, pyrazine, triazine, oxazine, oxathiazine, morpholine, azepine, oxepin, thiepin, and diazepine. Preferred heterocyclic rings are those having a single heteroatom present. Most preferred are those having a single nitrogen atom present.

Suitable substrates are commercially available or may be prepared by any means known in the art. For example U.S. Pat. No. 4,051,124 discloses a process for preparing 2,2'-azobis (2-methylpropanenitrile) by coupling 2-amino-2-methylpropanenitrile in the presence of a metal hypochlorite, water and a mixture of a quaternary ammonium compound and a nonionic or amphoteric surface active compound. U.S. Pat. No. 4,612,368 discloses a process for the preparation of 2,2'-azobis (2-methylbutanenitrile) in high yield by reacting 2-amino-2-methylbutanenitrile with a metal hypochorite in the presence of water and a mixture of surface active compounds at a temperature of about −10° C. to about 30° C. and recovering the 2,2'-azobis (2-methylbutanenitrile) from the reaction mixture. Commercial sources of suitable azobisnitrile substrates include Atochem Co., Three Parkway, Philadelphia, Pa. 19102; E. I. du Pont de Nemours and Company, Wilmington, Del. 19898; Japan Hydrazine Co. Inc., Nihon Hidorajin Kogyo KK, Iino Bldg. 1-1, Uchisaiwai-Cho, 2-Chome, Chiyoda-Ku, Tokyo 100 Japan, Otsuka Chemical Co., 6th Floor, Roman Ho Wood St., London, EC2Y5BA UK-England, and Wako Chemical Co., Richmond, Va.

Preferred for use in the present invention are azobisnitriles of formula I wherein $R_1$, $R_2$, $R_3$ and $R_4$ are each independently $C_1$–$C_8$ aliphatic hydrocarbon or $C_1$–$C_8$ aliphatic hydrocarbon substituted with carboxyl, hydroxyl, halogen, or —$OR_5$ wherein $R_5$ is a $C_1$–$C_4$ aliphatic hydrocarbon. More preferred are the azobisnitriles of formula I wherein $R_1$, $R_2$, $R_3$ and $R_4$ are each independently alkyl. Most preferred for use in the present invention are the substrates 2,2'-azobis(2-methylpropionitrile) of the formula $(CH_3)_2(CN)$ C—N=N—C (CN) $(CH_3)_2$ and 2,2'-azobis (2-methylbutyronitrile) of the formula $C_2H_5(CH_3)$ (CN) C—N=N—C(CN) $(CH_3)C_2H_5$.

Microorganisms suitable for use in the present invention include any species known to contain nitrile hydratase activity. Suitable genera may include, but are not limited to Rhodococcus, Pseudomonas, Alcaligenes, Arthrobacter, Bacillus, Bacteridium, Brevibacterium, Corynebacterium, and Micrococcus. In the present method preferred genera are Brevibacterium, Pseudomonas and Rhodococcus. Representative strains include Brevibacterium sp A4, *Pseudomonas putida* BTR 2034-3 and Rhodococcus sp. CM 1008. These latter two strains have been deposited with the American Type Culture Collection 12301 Parklawn Drive, Rockville, Md. 20852 USA on Dec. 15, 1994 and have been assigned ATCC Designations 55650 and 55651, respectively. Brevibacterium sp A4 (LMD 79.2) is available from Delft University of Technology, Kluyver Laboratory of Biotechnology, Julianalaan 67, 2628 BC, Delft, The Netherlands and is described in Jollegeas et al., C. R. Acad. Sci. Paris, 288, 655–658 (1979), herein incorporated by reference. The representative Pseudomonas and Rhodococcus strains show the following biochemical characteristics:

|  | BTR 2034-3 | CM 1008 |
| --- | --- | --- |
| Gram stain | − | + |
| Catalase | + | + |

CM 1008

(i) Produces acid from the following substrates after 21 days: fructose, glucose (open tube), inositol, mannitol, sorbitol, sucrose, trehalose.

(ii) Produces no acid from the following substrates after 21 days: adonitol, arabinose, cellobiose, dulcitol, erythritol, galactose, glucose (closed tube), glycerol, lactose, maltose, mannose, melibiose, melezitose, raffinose, rhamose, xylose.

(iii) Grows at 25° and 37° C., but not at 4° or 42° C.

(iv) Hydrolyses the following substrates: Tween 20®, Tween 80®, adenine, urea, tyrosine.

(v) Does not hydrolyze the following substrates: starch, cellulose, gelatin, hippurate, quanine, hypoxanthine, xanthine, casein.

(vi) Shows the following biochemical profile:
1) nitrate to nitrite reduction: negative,
2) Voges-Proskauer test: negative,
3) Indole test: negative,
4) McConkey's agar test: negative,
5) methyl red test: negative.

(vii) Shows morphological changes from a rods with elementary branching to irregular rods and cocci during the growth cycle.

(viii) Shows the presence of straight chain, unsaturated fatty acids and tuberculostearic acids in its membrane. BTR 2043-3

(i) Shows good growth in 48 hrs at 30° C. on the following carbon and energy sources:

Tween 40®, Tween 80®, D-fructose, α-D-glucose, D-mannose, methyl pyruvate, mono-methyl succinate, acetic acid, cis-aconitic acid, citric acid, formic acid, D-galacturonic acid, D-gluconic acid, D-glucuronic acid, b-hydroxybutyric acid, α-keto-glutaric acid, D,L-lactic acid, propionic acid, quinic acid, D-saccharic acid, succinic acid, bromosuccinic acid, glucuronamide, L-alanine, D-alanine, L-alyl-glycine, L-asparagine, L-aspartic acid, L-glutamic acid, L-histidine, hydroxy-L-proline, L-leucine, L-proline, L-pyroglutamic acid, L-serine, D,L-carnitine, γ-amino-butyric acid, inosine, phenethylamine, putrescine, 2-aminoethanol, glycerol.

(ii) Shows poor or no growth in 48 hrs at 30° C on the following carbon sources: α-cyclodextrin, dextrin, glycogen, N-acetyl-D-glucosamine, N-acetyl-D-galactosamine, aldonitol, L-arabinose, D-arabitol, cellobiose, i-erythritol, L-fucose, D-galactose, gentiobiose, m-inositol, α-d-lactose, lactulose, maltose, D-mannitol, D-melibiose, β-methyl-D-glucoside, D-psicose, D-raffinose, L-rhamnose, D-sorbitol, sucrose, D-trehalose, turanose, xylitol, D-galactonic acid lactone, D-glucosaminic acid, α-hydroxybutyric acid, p-hydroxyphenylacetic acid, itaconic acid, α-ketobutyric acid, α-ketovaleric acid, malonic acid, sebacic acid, succinamic acid, alaninamide, glycyl-L-aspartic acid, L-phenylalanine, D-serine, L-threonine, urocanic acid, uridine, thymidine, 2,3-butanediol, D,L-α-glycerol phosphate, glucose-1-phosphate, glucose-6-phosphate.

Methods for culturing bacteria suitable for the present invention are well known in the art and examples are given in *Manual of Methods for General Bacteriology*, Phillipp Gerhardt et al., eds), American Society for Microbiology, Washington, D.C. (1981). Typically, bacteria are grown on basal media containing yeast extract and glucose at temperatures of about 25° C. to 30° C. with shaking Enzyme activity in the preferred bacterial strains of the present invention is induced by growth media containing a spectrum of nitriles. For the purposes of the present invention acetonitrile, butyronitrile and benzonitrile were used. This combination was used as a way of ensuring maximum induction of any nitrile hydrolyzing enzyme system present in the organisms.

Briefly, enzyme induction involves contacting an actively growing culture with a suitable amount of nitrile mixture and growing the culture from between 24 hr to 72 hr. Concentrations of nitrile in the growth media may range from 0.5 mM to 25 mM. A concentration of 6 mM is preferred. At the end of the growth period the cells are harvested, washed with 15% glycerol in 50 mM phosphate buffer, pH 7.2 and stored, frozen, −70° C. until use Microorganisms can be used as intact cells, or preferably as immobilized whole cell catalysts. Any method of immobilizing cells which is known in the art and which does not substantially reduce hydratase activity can be utilized. Preferred methods include, but are not limited to immobilization in agarose, alginate or polyacrylamide. For a discussion on cell immobilization see Gerhardt, P., et al., supra.

Preferred azobisnitriles are treated in aqueous suspension at temperatures from about 3° C. to about 35° C. at near neutral pH of about 6–9. Following the addition of the microorganism to the suspension, the suspension is gently mixed until such time as the desired product is formed. The product can then be separated from the aqueous suspension by extraction into a suitable solvent, for example methylene chloride, ethyl acetate, or chlorform. Either the cyanoamide (addition of 1 mole of water per mole of azobisnitrile) or diamide (addition of 2 moles water per mole of azobisnitrile) may be produced. Each addition of water substantially improves the water solubility of the product.

The process of the present invention is useful to produce cyanoamide and diamide derivatives of azobisnitriles. These enzymatic hydrolysis products are useful as free radical polymerization initiators in emulsion, dispersion and solution polymerization systems. Polymerizations involving vinyl chloride, methyl methacrylate, and butadiene-styrene are examples of such systems in industry that would benefit from the use of such initiators.

EXAMPLES

General Methods

Bacterial selection and growth

Bacteria useful in the present invention were grown in a nutrient medium as described below:

| 4Y (low yeast) Basal Medium | |
|---|---|
| Component | g/L |
| HH2PO4 | 8.85 |
| Sodium citrate | 0.225 |
| MgSO4.7H2O | 0.5 |
| FeSO4.4H2O | 0.05 |
| FeCl2.4H2O | 0.0015 |
| CoCl2.6H2O | 0.0002 |
| MnCl2.4H2O | 0.0001 |
| ZnCl2 | 0.00007 |
| H3BO3 | 0.000062 |
| NaMoO4.2H2O | 0.000036 |
| NiCl2.6H2O | 0.000024 |
| CuCl2.2H2O | 0.000017 |
| yeast extract | 0.010 |
| glucose | 10 |

For development of nitrile hydrolyzing enzyme activity, the following nitrile amendments were made to the 4Y (low yeast) basal medium:

| Strain | Nitrile | Concentration, mM |
|---|---|---|
| BTR 2034-3 | acetonitrile | 6 mM |
| | + butyronitrile | 6 mM |
| | + benzonitrile | 6 mM = Total 18 mM |
| CM 1008 | acetonitrile | 6 mM |
| | + butyronitrile | 6 mM |
| | + benzonitrile | 6 mM = Total 18 mM |

All bacterial isolates were grown from frozen stocks preserved with 15% glycerol. One tenth of a milliliter of the frozen stock containing a cell suspension at an optical density of 0.2 or greater at 490 nm was inoculated into 10 ml of 4Y (low yeast) basal medium plus nitrile as indicated above. The cells were allowed to grow from 24–72 hours at 28° C. on a rotary shaker at 250 rpm. Cells were then transferred to 1 liter of fresh medium. Following 24–72 hours of additional growth, the cells were harvested by centrifugation and washed once with a 10% glycerol solution in 50 mM potassium phosphate buffer, pH 7.2. The wash solution was removed and the cells were immediately frozen on dry ice. Frozen cell material was stored at −60° C. until used for hydrolysis of the azobisnitriles.

Hydrolysis Product Analysis

Presence of the cyanoamide or diamide azobisnitrile derivatives were analyzed by the following methods.

The azobisnitrile substrate and hydrolysis products were extracted for analysis by high pressure liquid chromatography (HPLC). For extraction, 15 μl of 3M sulfuric acid ($H_2SO_4$) was added to acidify the reaction volume to pH 2–3. Four milliliters of methylene chloride was then added to the reaction vial which was then shaken at 28° C. for ½ hour at approximately 350 rpm. The two chemical phases were then separated by a short centrifugation. The bottom methylene chloride layer containing the substrate and products was removed. The methylene chloride phase was placed in a new vial and dried under nitrogen ($N_2$). The residue was frozen at −20° C. to await analysis. Immediately before HPLC analysis, the residue was dissolved in 0.5 ml of acetonitrile.

HPLC analysis was performed with a Zorbax® ODS reverse phase column, 4.6 mm×150 mm. To elute the compounds of interest, the following mobile phase gradients were used: (1) for AZMPN, AZMPNAm, AZMPAm— Started at acetonitrile:water (109:891) with a linear increase to acetonitrile:water (406:594) at twenty minutes followed by a linear decrease back to acetonitrile:water (109:891) at twenty five minutes; (2) for AZMBN, AZMBNAm, AZMBAm—Started at acetonitrile:water (159:841) with a linear increase to acetonitrile:water (554:446) at twenty five minutes followed by a linear decrease back to acetonitrile:water (159:841) at thirty minutes. Azo products were detected by UV adsorption at 345 nm. Peak identities were based on coelution with known standards, along with mass spectral (MS) or nuclear magentic resonance spectroscopic (NMR) analysis.

| Compound | Retention time |
|---|---|
| AZMPN | 21 minutes |
| AZMPNAm | 12.5 minutes |
| AZMPAm | 5.5 minutes |
| AZMBN | 25.8 minutes |
| AZMBNAm | 16.9 minutes |
| AZMBAm | 7.025–8.005 minutes, (split peak due to meso form eluted at a slightly |

| Compound | Retention time |
|---|---|
| | different retention time vs. the racemic mix of R,R and S,S stereoisomers) |

Example 1

Hydrolysis of AZMPN to AZMPNAM by Pseudomonas Putida BTR 2034-3

Fifty milligrams wet cell paste of Pseudomonas putida strain BTR 2034-3 was suspended in 1 ml of 100 mM potassium phosphate buffer, pH 7.2. The suspension was added to a glass vial containing 8.6 mg of AZMPN. The suspension was agitated at 250 rpm at 25° C. After 48 hrs, approximately 15 µl of 3M sulfuric acid $H_2SO_4$ was added to acidify the aqueous suspension to pH 2–3. Methylene chloride, 4 ml, was added and the combined phases were shaken for ½ hour at approximately 350 rpm. The methylene chloride phase was removed and dried under a $N_2$ stream. Analysis of the reaction products in the extract by high pressure liquid chromatography revealed the formation of 5.1 mg AZMPNAm product with 3.2 mg AZMPN substrate remaining.

Example 2

Hydrolysis of AZMPN to AZMPNAM by Rhodococcus SP. CM 1008

Fifty milligrams wet cell paste of Rhodococcus CM 1008 was suspended in 1 ml of 100 mM potassium phosphate buffer, pH 7.2. The suspension was added to a glass vial containing 8.6 mg of AZMPN. The suspension was agitated at 250 rpm at 25° C. After 48 hrs, approximately 15 µl of 3M sulfuric acid $H_2SO_4$ was added to acidify the aqueous suspension to pH 2–3. Methylene chloride, 4 ml, was added and the combined phases were shaken for ½ hour at approximately 350 rpm. The methylene chloride phase was removed and dried under a $N_2$ stream. Analysis of the reaction products in the extract by high pressure liquid chromatography revealed the formation of 2.7 mg AZMPNAm product with 2.8 mg AZMPN substrate remaining.

Example 3

Hydrolysis of AZMBN to AZMBAm and AZMBNAm by Pseudomonas Putida BTR 2034-3

Fifty milligrams wet cell paste of Pseudomonas putida strain BTR 2034-3 was suspended in 1 ml of 100 mM potassium phosphate buffer, pH 7.2 and added to a glass vial containing 4.8 mg of AZMBN. The suspension was agitated at 250 rpm at 25° C. After 48 hrs, approximately 15 µl of 3M sulfuric acid $H_2SO_4$ was added to acidify the aqueous suspension to pH 2–3. Methylene chloride, 4 ml, was added and the combined phases were shaken for ½ hour at approximately 350 rpm. The methylene chloride phase was removed and dried under a $N_2$ stream. Analysis of the reaction products in the extract by high pressure liquid chromatography revealed the formation of 3.9 mg of AZMBAm product and 1.4 mg AZMBNAm product with 0.08 mg substrate remaining.

Example 4

Hydrolysis of AZMBN by Immobilized Cells pf Brevibacterium Sp. A4

Brevibacterium sp. A4 was obtained from Delft University of Technology, Faculty of Chemical Technology and Materials Science, Kluyver Laboratory of Biotechnology, Julianalaan 67, 2628 BC Delft, The Netherlands. It is a mutant derived from Brevibacterium sp. R312 which lacks wide-spectrum amidase activity, as described by Jallegeas, J. C. et al. 1979, C. R. Acad. Sci. Paris. 288: 655–658.

Brevibacterium sp. strain A4 was grown under culture conditions adapted from Bernet, N., A. Arnaud, & P. Galzy. 1990. Biocatalysis. 3:259. The growth was initiated with a 1 ml 15% glycerol frozen inoculum in a 50 ml shake flask at 30° C. containing 20 ml of medium in deionized water (Hydro ultrapure water system) consisting of 50 mM $HPO_4^{2-}$ ($K_2HPO_4$, pH 7.2), 36 µM Fe (as an Fe.Citrate solution with 0.10M $FeSO_4$ and 0.5M citric acid at pH 6.5), 44 µM thiamine.HCl 2.0 mM $MgSO_4$, 75 mM $NH_4Cl$, 1% (w/v) dextrose, 0.40 µL of acetonitrile and 4 µL of a trace element solution consisting of 0.8% con. HCl, 6 mM Fe (as Fe.Citrate solution), 1.5 mM $MnCl_2$, 0.38 mM $NiSO_4$, 0.40 mM $CuSO_4$, 0.43 mM $ZnSO_4$, 1.6 mM $H_3BO_3$, 0.18 mM $NaMoO_4$, 0.12 mM KI, and 0.16 mM KBr. 15 ml of this culture was used to innoculate a 2 L shake flask containing 1 L of the previously described media (using 2 ml of acetonitrile and 200 µL of the trace element solution).

The 1 L shake flask was used to innoculate a 40 L New Brunswick Scientific mobile pilot plant fermenter containing 30 L of a growth media like the one previously described with the following changes: 1 ml of the trace metals solution, 50 µM Fe, 150 mM $NH_4Cl$, 5.7 mM NaCl, 10 ml antifoam, and 75 ml acetonitrile. The 30 L fermenter growth was then used to innoculate a 400 L New Brunswick Scientific fermentation system containing 270 L of a growth media similar to the 30 L fermenter media with the following changes: 18 mM $HPO_4^{2-}$ ($K_2HPO_4$, pH 7.2) and 70 mM $(NH_4)_2SO_4$ (instead of $NH_4Cl$). The pH of the growth was maintained at 7.0 using 50% $NH_4OH$ solution and concentrated $H_3PO_4$. The growth was monitored by 660 nm turbidity measurements, typically harvested at an optical density of 8–10 at about 25–30 hours, and yielded about 8 g of cell paste/L (wet wt.). Cells were concentrated by centrifugation and stored frozen at −80° C.

To immobilize the cells 25 g of wet cells were mixed with 100 cc of a solution of 2.28% sodium alginate in 20 mM sodium butyrate pH 7.1 at 5° C. This suspension was pumped through a 1 mm diameter orifice into 500 cc of 0.1M $CaCl_2$, 20 mM sodium butyrate, pH 7.1 at 5° C. The resulting suspension of approximately 2 mm diameter calcium alginate particles were allowed to harden for two hours, and then filtered to recover the particles. The particles were washed four times with a total of approximately 500 cc of 5° C. 5 mM $CaCl_2$ 20 mM sodium butyrate pH 7.1 buffer and stored at 5° C. in 500 cc of that buffer.

Approximately 1.2 g of wet beads was suspended in 10 mls of 5 mM $CaCl_2$ 20 mM sodium butyrate pH 7.1 buffer. This suspension was poured into a 20 ml glass vial containing 4.8 mg of AZMBN dispersed on 0.5 g of 0.5 mm glass beads. The suspension was shaken at 100 rpm at room temperature for 66 h. The suspension was then acidified to pH 2–3 by the addition of 0.015 ml 3N sulfuric acid. AZMBN and hydrolysis products were extracted from the suspension by the addition of 8 ml of methylene chloride followed by 0.5 h of shaking at 350 rpm at room temperature. The methylene chloride phase is then removed and dried under an $N_2$ stream. Analysis by high pressure liquid chromatography revealed the following compounds on a relative weight basis: 66% AZMBNAm, 31% AZMBam, 3% AZMBN.

What is claimed is:

1. A process for the enzymatic conversion of an azobisnitrile to a more water soluble cyanoamide or diamide derivative without destroying the N=N bond, the azobisnitrile having formula I:

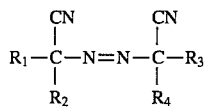

wherein, $R_1$, $R_2$, $R_3$ and $R_4$ independently of each other are
  a) unsubstituted $C_1$–$C_8$ aliphatic hydrocarbon;
  b) $C_1$–$C_8$ aliphatic hydrocarbon substituted with carboxyl, hydroxyl, halogen, or $OR_5$ wherein $R_5$ is a $C_1$–$C_4$ aliphatic hydrocarbon;
  c) $C_3$–$C_8$ alicyclic hydrocarbon;
  d) $C_3$–$C_8$ alicyclic hydrocarbon substituted with alkyl or halogen;
  e) $C_4$–$C_{10}$ aromatic hydrocarbon substituted with halogen or nitro; or
  f) a five or six membered heterocyclic ring containing O, S or N atoms; or $R_1$ and $R_2$ are taken together to form a $C_4$–$C_{12}$ alicyclic hydrocarbon and $R_3$ and $R_4$ are as defined above; or $R_3$ and $R_4$ are taken together to form a $C_4$–$C_{12}$ alicyclic hydrocarbon and $R_1$ and $R_2$ are as defined above, said process comprising:

1) contacting an aqueous suspension of an azobisnitrile of formula I with a microorganism having nitrile hydratase activity and incapable of degrading N=N bonds selected from the group consisting of Rhodococcus, Pseudomonas and Brevibacterium; and
2) recovering either a cyanoamide of formula II

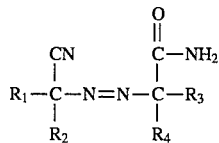

wherein $R_1$, $R_2$, $R_3$ and $R_4$ are defined as above for formula I, or a diamide of formula III

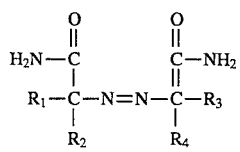

wherein $R_1$, $R_2$, $R_3$ and $R_4$ are defined as above for formula I.

2. The process of claim 1 wherein said microorganism is *Pseudomonas putida* BTR 2034-3.

3. The process of claim 1 wherein said microorganism is Rhodococcus sp. CM 1008.

4. The process of claim 1 wherein said microorganism is Brevibacterium sp A4.

5. The process of claim 1 wherein the microorganism is a whole cell or an immobilized whole cell.

6. The process of claim 1 wherein for formulae I, II and III each $R_1$, $R_2$, $R_3$ and $R_4$ is independently of each other
  $C_1$–$C_8$ aliphatic hydrocarbon; or
  $C_1$–$C_8$ aliphatic hydrocarbon substituted with carboxyl, hydroxyl, halogen, or
  —$OR_5$ wherein $R_5$ is a $C_1$–$C_4$ aliphatic hydrocarbon.

7. The process of claim 6 wherein for formulae I, II and III, each $R_1$, $R_2$, $R_3$ and $R_4$ is independently of each other an alkyl group.

8. The process of claim 6 wherein said formula I is 2,2'-azobis (2-methylbutyronitrile) or 2,2'-azobis (2-methylpropionitrile).

9. The process of claim 6 wherein said formula II is 2(2-azo-2-methylpropionitrile)-2-methylpropionamide or 2(2-azo-2-methylbutyronitrile)-2-methylbutyramide.

10. The process of claim 6 wherein said formula III is 2,2'-azobis(2-methylpropionamide) or 2,2'-azobis(2methylbutyramide).

11. The process of claim 1 wherein prior to step 1) said microorganism is contacted with a growth media containing a mixture of nitriles comprising acetonitrile, a $C_4$–$C_9$ aliphatic nitrile and an aromatic nitrile.

12. The process of claim 11 wherein the mixture of nitriles consists of acetonitrile, butyronitrile, and benzonitrile.

13. A process for the enzymatic conversion of an azobisnitrile to a more water soluble cyanoamide or diamide derivative without destroying the N=N bond, the azobisnitrile having formula I:

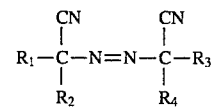

wherein, $R_1$, $R_2$, $R_3$ and $R_4$ independently of each other are
  a) unsubstituted $C_1$–$C_8$ aliphatic hydrocarbon;
  b) $C_1$–$C_8$ aliphatic hydrocarbon substituted with carboxyl, hydroxyl, halogen, or $OR_5$ wherein $R_5$ is a $C_1$–$C_4$ aliphatic hydrocarbon;
  c) $C_3$–$C_8$ alicyclic hydrocarbon;
  d) $C_3$–$C_8$ alicyclic hydrocarbon substituted with alkyl or halogen;
  e) $C_4$–$C_{10}$ aromatic hydrocarbon substituted with halogen or nitro; or
  f) a five or six membered heterocyclic ring containing O, S or N atoms; or $R_1$ and $R_2$ are taken together to form a $C_4$–$C_{12}$ alicyclic hydrocarbon and $R_3$ and $R_4$ are as defined above; or $R_3$ and $R_4$ are taken together to form a $C_4$–$C_{12}$ alicyclic hydrocarbon and $R_1$ and $R_2$ are as defined above, said process comprising:

1) contacting an aqueous suspension of an azobisnitrile of formula I with a microorganism having nitrile hydratase activity and incapable of degrading N=N bonds selected from the group consisting of Rhodococcus, Pseudomonas and Brevibacterium, said microorganisms capable of converting the azobisnitrile of formula I to a cyanoamide or diamide without destroying the azo fuctionality when grown in a medium in the presence of a mixture of nitriles comprising acetonitrile, a $C_4$–$C_9$ aliphatic nitrile and an aromatic nitrile; and 2) recovering either a cyanoamide of formula II

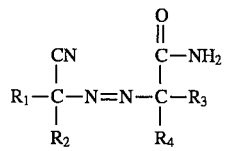

wherein $R_1$, $R_2$, $R_3$ and $R_4$ are defined as above for formula I, or a diamide of formula III

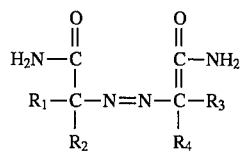

wherein $R_1$, $R_2$, $R_3$ and $R_4$ are defined as above for formula I.

* * * * *